United States Patent [19]

Bodor et al.

[11] 4,340,603
[45] Jul. 20, 1982

[54] NOVEL INOTROPIC PRODRUGS

[75] Inventors: Nicholas S. Bodor; Kenneth B. Sloan, both of Gainesville, Fla.; Stefano A. Pogany, Lawrence, Kans.

[73] Assignee: INTERx Research Corporation, Lawrence, Kans.

[21] Appl. No.: 177,824

[22] Filed: Aug. 13, 1980

[51] Int. Cl.³ .................... A61K 31/265; C07C 69/76; C07C 69/74; C09F 5/08
[52] U.S. Cl. ................................ 424/301; 260/455 R; 260/410.5; 560/109; 560/121; 560/123; 560/128; 560/138; 564/374; 564/381
[58] Field of Search ...................... 260/455 R, 410.5; 560/109, 121, 123, 128, 138; 424/301; 564/374, 381

[56] References Cited

PUBLICATIONS

Chem. Abstracts, 85:424w, vol. 85, p. 419, 1976.
Burger, Medicinal Chemistry, Interscience Pub., Inc., NY, 1960, pp. 330-337 and 349-355.

Primary Examiner—John M. Ford
Assistant Examiner—Robert C. Whittenbaugh
Attorney, Agent, or Firm—Burns, Doane, Swecker & Mathis

[57] ABSTRACT

Novel, transient inotropic prodrug forms of the N-(2-phenylethyl)-ω-phenylalkylamines, notably of dobutamine, have (i) the structural formula (I):

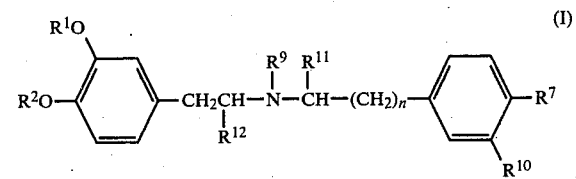

with the proviso that at least one $R^1$, $R^2$ or $OR^1$, when $R^7$ and/or $R^{10}$ is $OR^1$, must be $R^3COXCH(R^4)$— or $R^3COXCH(R^4)O$—, respectively.

28 Claims, No Drawings

NOVEL INOTROPIC PRODRUGS

CROSS-REFERENCE TO RELATED APPLICATIONS

Our copending application, Ser. No. 108,055, filed Dec. 28, 1979, hereby expressly incorporated by reference in its entirety and relied upon. Cf. our related copending application Ser. No. 114,205, filed Jan. 22, 1980, hereby also expressly incorporated by reference in its entirety and relied upon.

BACKGROUND OF THE INVENTION

1. Field of the Invention

The present invention relates to novel, transient prodrug derivatives of the inotropic N-(2-phenylethyl)-ω-phenylalkylamines, notably of dobutamine, and, more especially, relates to certain acyl-X-methylether latentiated forms of such dobutamine nucleus or congeners thereof [hereinafter such basic nuclei shall collectively simply be deemed "dobutamine"].

As employed in this application, the expression "prodrug" denotes a derivative of a known and proven prior art compound, which derivative, when absorbed into the bloodstream of a warm-blooded animal, "cleaves" in such a manner as to release the proven drug form and permits the same to attain a higher bioavailability level than that which could be obtained if the proven drug form, per se, was administered.

Furthermore, also as used in this application, the term "transient" denotes "cleavage" of the compounds of this invention in such a manner that the proven drug form is released and the remaining "cleaved" moiety is non-toxic and metabolized in such a manner that non-toxic, metabolic products are produced.

2. Description of the Prior Art

It is well known to this art that dobutamine, and its salts, are useful active agents for the treatment or management of certain cardiac disease states, e.g., same are useful cardiotonic agents. See generally *The Merck Index*, page 3410 Ninth Edition (1976); U.S. Pat. No. 3,987,200 to Tuttle et al.

Nevertheless, it too is known to the art that dobutamine, and the various art-recognized therapeutically active derivatives thereof, are characterized by certain inherent disadvantages, notably serious bioavailability and physiological availability problems upon administration, e.g., rapid inactivation in a biological system. Such reduced availability can be attributed in part to poor lipid solubility [by reason of the presence of the hydrophilic phenolic hydroxy groups], and also to metabolic losses during and following conventional administration. Other disadvantages associated with the prior art compounds are instability to both air and light, and same are subject to chemical attack by many agents that are conventionally used in pharmaceutical preparations, as well as a variety of other unfavorable pharmacodynamic properties. Also, for certain applications, relatively high concentrations of drug are required.

Thus, there exists a clear and present need for novel latentiated forms of dobutamine, which derivatives would be conspicuously devoid of those disadvantages and drawbacks that to date have characterized the prior art compounds.

SUMMARY OF THE INVENTION

Accordingly, a major object of the present invention is the provision of a novel class of inotropic dobutamine prodrugs.

Another object of this invention is the provision of a novel class of inotropic dobutamine prodrugs that is essentially free from the unwanted effects associated with the prior art.

Still another object of the invention is to provide a new and useful class of latentiated dobutamine species which is characterized by enhanced stability and solubility, can be administered in standard pharmaceutical formulations to warmblooded animals to elicit a local, topical or systemic physiological or pharmacological beneficial effect, and which exhibits enhanced bioavailability and physiological availability.

Yet another object is to provide a novel class of inotropic dobutamine prodrugs which will elicit a more effective sympathomimetic response, at lower concentrations or dosage levels, than its parent molecules.

Other objects, features and advantages of the invention will be apparent to those skilled in the art from the detailed description of the invention which follows.

DETAILED DESCRIPTION OF THE INVENTION

More particularly according to this invention, all of the aforenoted objects, features and advantages thereof are provided by the novel dobutamine (i) prodrugs having the structural formula (I):

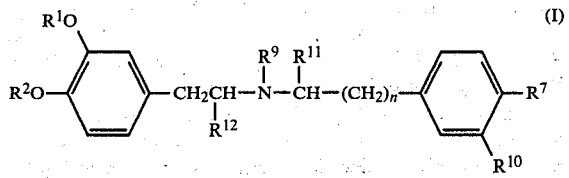

wherein $R^1$ and $R_2$ are independently selected from the group consisting of hydrogen, $R^3$—CO— and

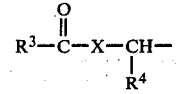

wherein X is O, S or $NR^5$; $R^3$ is selected from the group consisting of straight or branched chain alkyl having from 1 to 20 carbon atoms; aryl having from 6 to 10 carbon atoms; cycloalkyl having from 3 to 8 carbon atoms; alkenyl having from 2 to 20 carbon atoms; cycloalkenyl having from 4 to 8 carbon atoms; alkynyl having from 2 to 20 carbon atoms; aralkyl, alkaryl, aralkenyl, aralkynyl, alkenylaryl, alkynylaryl, loweracyloxyalkyl, and carboxyalkyl, wherein alkyl, aryl, alkenyl and alkynyl are as defined above; saturated or unsaturated monoheterocyclic or polyheterocyclic, or fused heterocyclic, containing from 1 to 3 of any one or more of the hetero atoms N, S or O in each heterocyclic ring thereof and each such ring being from 3- to 8-membered; and mono- or polysubstituted derivatives of the above, each of said substituents, $R^8$, being select from the group consisting of lower alkyl (e.g., having from 1 to 8 carbons, preferably 1 to 4 carbons), lower alkoxy, lower acyl, lower acyloxy, halo, haloloweralkyl, cyano, lower alkoxycarbonyl, loweralkylthio, amino, nitro, loweralkylamino, diloweralkylamino, carboxyl, carbamyl, loweralkylcarbamyl, diloweralkylcarbamyl and

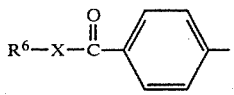

wherein $R^6$ is hydrogen or alkyl having from 1 to 10 carbons; $R^4$ is hydrogen, lower acyl, cyano, halolower-alkyl, carbamyl, loweralkylcarbamyl, diloweralkylcarbamyl, —CH$_2$ONO$_2$, —CH$_2$OCOR$^3$, or any non-heterocyclic member of the group defined by $R^3$ above; $R^5$ is hydrogen or lower alkyl; $R^7$ and $R^{10}$ are hydrogen, OR$^1$ or $R^8$; $R^9$ is hydrogen, lower alkyl, COCF$_3$, COOC(CH$_3$)$_3$, COOCH$_2$C$_6$H$_5$, or other N-protective group conventional to amino acid chemistry; $R^{11}$ and $R^{12}$ are hydrogen or methyl; n is 1 or 2; with the proviso that at least one $R^1$, $R^2$ or OR$^1$, when $R^7$ and/or $R^{10}$ is OR$^1$, must be R$^3$COXCH(R$^4$)— or R$^3$COXCH(R$^4$)O—, respectively; (ii) prodrugs having the structural formula (I) wherein at least one $R^3$CO— moiety comprising at least one $R^1$, $R^2$ or OR$^1$, when $R^7$ is OR$^1$, is the residue of any naturally occurring protein amino acid, the residue of any N-substituted naturally occurring amino acid, which N-substituent is lower alkyl or any amino acid protective group cleavable via hydrogenolysis or hydrolysis, or the residue of an N,N-lower dialkyl or C$_4$-C$_7$ cycloalkylamino acid; and (iii) the non-toxic, pharmaceutically acceptable salts thereof.

Most preferably according to this invention, n is 2, $R^{11}$ is methyl, $R^9$ and $R^{12}$ are hydrogen, and either $R^7$ or $R^{10}$ is hydrogen with the other (preferably the $R^7$) being a member selected from the group consisting of OR$^1$, aminocarbonyl, methylaminocarbonyl, methoxycarbonyl and ethoxycarbonyl. Similarly most preferably, either or both of $R^1$ and $R^2$ comprises an R$^3$COXCH(R$^4$)- function; and when $R^{10}$, but not $R^7$, is hydrogen, then $R^{11}$ should be methyl.

The term "naturally occurring protein amino acid" includes without limitation:

| | |
|---|---|
| Glycine | Arginine |
| Alanine | Lysine |
| Valine | Hydroxylsine |
| Leucine | Phenylalanine |
| Isoleucine | Tyrosine |
| Cysteine | Asparagine |
| Cystine | Glutamine |
| Methionine | Proline |
| Serine | Hydroxyproline |
| Threonine | Histidine |
| Aspartic acid | Tryptophan |
| Glutamic acid | Pyroglutamic acid |

Similarly, the import of the phase "amino acid protective group 'cleavable' via hydrogenolysis or hydrolysis" can be further gained from a review of U.S. Pat. No. 3,803,102 to Felix and U.S. Pat. No. 3,957,803 to Bodor, et al.

It too will be appreciated that by "residue" of a naturally occurring amino acid there are intended not only those species wherein the "CO" of the R$^3$—CO— moiety comprising the topic prodrugs is the carbonyl function originating from the amino acid, per se, e.g., species of the type wherein at least one OR$^1$, OR$^2$, $R^7$ or $R^{10}$ is:

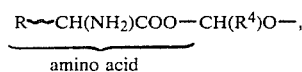

but also such species including a free carboxyl function, e.g., species of the type:

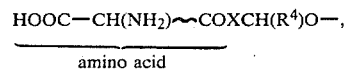

as well as amino acid species of amido type, wherein the —CONHR$^5$ function comprises the parent amino acid, e.g., species of the type:

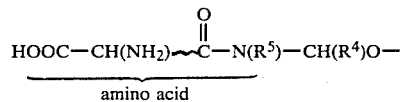

When R$^3$ comprises a heterocyclic function, representative such heterocycles, include, without limitation, and without regard to the point of attachment on the ring, piperazinyl, 4-methylpiperazinyl, pyridinyl, pyrazinyl, pyrimidinyl, pyridazinyl, pyrazolyl, pyrrolyl, pyrrolidinyl, pyrrolinyl, pyrazolinyl, pyrazolidinyl, piperidyl, morpholinyl, quinuclidinyl, isoindolinyl, indolinyl, thienyl, benzothienyl, napthothienyl, thianthrenyl, furyl, pyranyl, chromenyl, xanthenyl, phenoxathiinyl, imidazolyl, pyridyl, indolizinyl, isoindolyl, 3H-indolyl, indolyl, indazolyl, purinyl, phthalazinyl, quinolyl, isoquinolyl, 4H-quinolizinyl, quinoxalinyl, naphthyridinyl, cinnolinyl, pteridinyl, carbazolyl, 4aH-carbazolyl, β-carbolinyl, phenanthridinyl, acridinyl, perimidinyl, phenoxazinyl, furazanyl, isochromanyl, chromanyl, imidazolinyl, 1-methyl-azarinyl, 1-methyl-pyrrolyl, 1-methyl-imidazolyl, 1-methyl-pyrazolyl, 2-methyl-isoindolyl, 3H-indolyl, phtalazinyl, quinoxilinyl, quinazidinyl, phenazinyl, isothiazolyl, 10-methylphenothiazinyl, isoxazolyl, furazanyl, the various saturated, unsaturated or partially saturated congeners of any of the above, and those attached to the carbonyl carbon via a lower alkylene bridge.

By "pharmaceutically acceptable salt," there are intended the conventional non-toxic salts or the quaternary ammonium salts of the compounds of the formula (I) formed e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, toluenesulfonic, and the like.

The pharmaceutically acceptable salts of the present invention can be synthesized from the compounds embraced by formula (I) by conventional chemical methods. Generally, the salts are prepared by reacting the free base with stoichiometric amounts or with an excess of the desired salt forming inorganic or organic acid in a suitable solvent or various combinations of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, a symmetrical or asymmetrical ether containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt or spontaneous separation from the solution, or it can be precipitated by the addition of a solvent in which the salt is insoluble and recovered therefrom.

Examples of suitable inorganic and organic solvents for performing the various reactions include any inorganic or organic solvent that does not adversely affect the reactants or the resulting product, including halogenated solvents such as methylene chloride, chloroform, carbon tetrachloride, ethylene chloride, ether solvents such as diethyl ether, dimethyl ether, and other solvents such as tetrahydrofuran, dioxane, diglyme, n-hexane, cyclooctane, benzene, heptane, cyclohexane; mixtures thereof, and like aliphatic, cycloaliphatic and aromatic hydrocarbon solvents, water, acidified aqueous solutions, mixed organic and inorganic solutions; ethyl acetate, propyl acetate, and the like.

The "quaternary ammonium sats" are likewise conventional to the pharmaceutical arts, and these too are prepared via typical methodology. Moreover, either the $R^3$ moiety, or the parent nucleus, or both, of the subject prodrug molecules can be quaternized or otherwise comprise a salt function.

The compounds of the present invention are conveniently prepared via the following general syntheses:
Synthetic Scheme:

In a first step, the amine function of dobutamine is suitably protected, e.g., with a t-butyloxycarbonyl protective group by reaction with t-butylazidoformate, in the presence of base, e.g., triethylamine or N-methylmorpholine, in a polar aprotic solvent, e.g., dioxane, THF or dichloromethane, under atmospheric pressure and at a temperature of from $-20°$ C. to the boiling point of the solvent, preferably from $0°$ C. to $20°$ C. Next, the N-t-butoxycarbonyl dobutamine which results is reacted, under $S_N2$ conditions, with 3-6 equivalents of a compound of the formula:

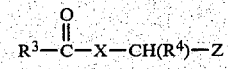

wherein X, $R^3$ and $R^4$ are as above defined and Z is suitable leaving group, e.g., chloride, bromide, tosylate, etc., and preferably the iodide, in the presence of 2-4 equivalents of e.g., potassium carbonate in a ketone solvent, e.g., acetone, methylethylketone, cyclohexanone, 2-pentanone, 3-hexanone, or the like, to form a compound having the structural formula:

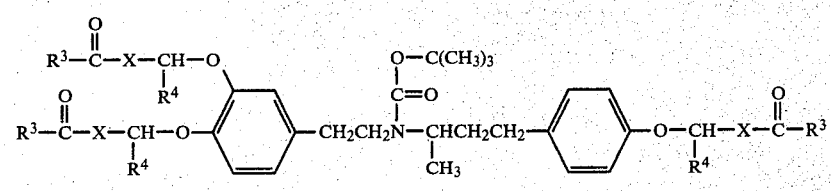

The t-BOC protective group is thence removed by protonation with HA, e.g., with HCl in ethyl acetate, or trifluoroacetic acid in dichloromethane or tetrahydrofuran, or any "other" common reagent for removing the t-BOC protective group in amino acid chemistry, to result in the compound according to the invention:

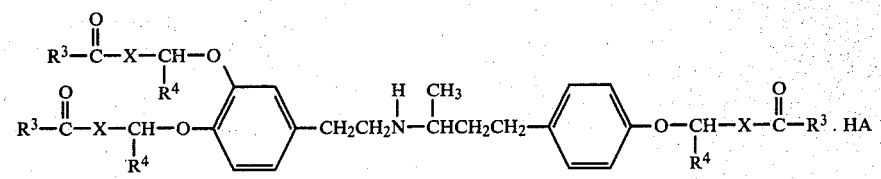

from which the monoacyl-X-methylether derivative, namely:

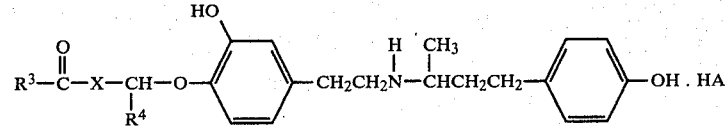

or the other isomeric forms, or a mixture of such isomeric forms, may be prepared, via simple partial hydrolysis. Likewise, the diacyl-X-methylether derivatives, and isomers thereof, may be prepared, e.g.:

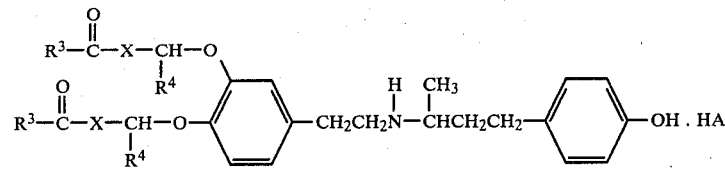

The monoacyl and diacyl derivatives may also be prepared simply by utilizing much lesser amounts of the $R^3COXCH(R^4)$—Z reactant.

The reactant

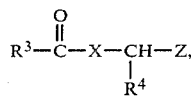

wherein X is either O, S or $NR^5$, is prepared thus:

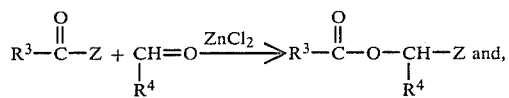

(i)

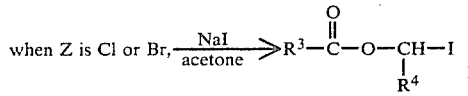

(ii)

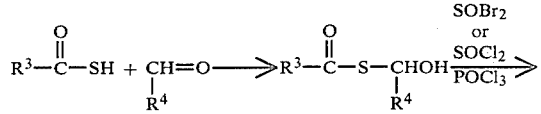

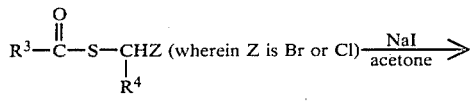

or

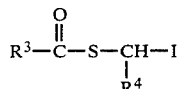

(iii)

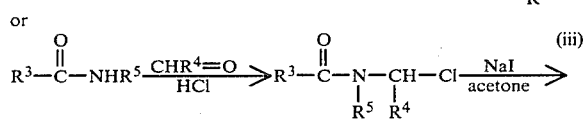

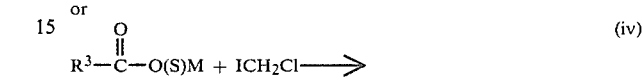

e.g.,

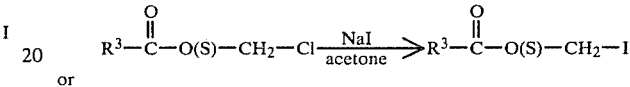

wherein $R^{13}$ and R' are protective groups, e.g., R' = $C_6H_5$—$CH_2$—O—CO—, $R^{13} = \phi$—$CH_2$— or

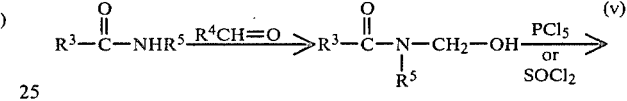

(iv)

or (v)

Other suitable N-protective groups, i.e., other than t-butoxycarbonyl or t-BOC protective group, include N-formate, carbobenzyloxy, —$CH_2$—S—R, —$COCF_3$, —$C(CH_3)$=C=$COCH_3$, any completely protected peptide, e.g., —CO—CH(R)NHCH=O, =CH—$C_6H_4$-(m—OH), and the like. Similarly, the hydroxyl function comprising the 4-hydroxyphenyl end of the molecule too may be protected, e.g., by lower acylation. The N-protected or O-protected compounds, thus, not only are useful intermediates, but are also useful final products, also demonstrating the utility of the parent drug species.

A representative synthetic scheme, thus, would include:

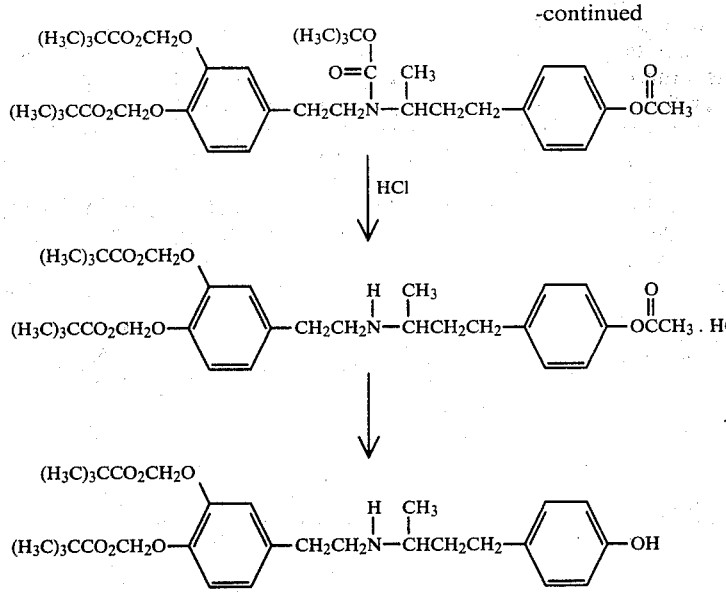

Moreover, depending on whether $S_N^1$ of $S_N^2$ conditions are employed, both the polyacyl-X-methylether derivatives, or the partially acylated, partially acyl-X-methylated derivatives, or isomers, may be prepared; see generally our aforenoted copending application, Ser. No. 108,055, but substituting dobutamine or congeners thereof for the starting materials in the synthetic schemes "B" and "C".

While all of the compounds according to the invention are characterized by good lipid solubility and high bioavailability, are quite stable to both air and light, and are more immune to chemical attack by those agents which are conventionally used in pharmaceutical preparations, the same are nonetheless facilely chemically and/or enzymatically metabolized/hydrolyzed at their therapeutic sites of action, i.e., upon administration are cleaved into the known and proven parent dobutamine molecule, per se, as well as into various non-toxic products of metabolism/hydrolysis, according to the following general scheme:

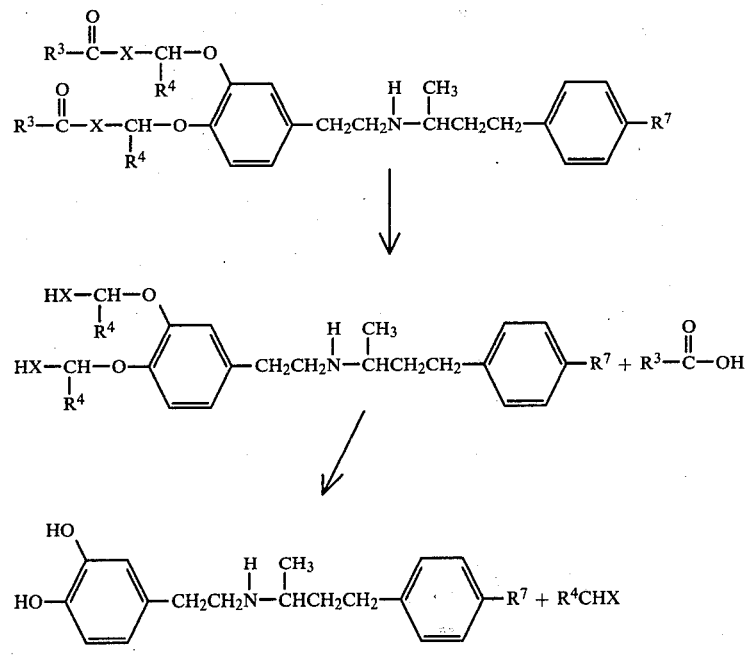

It will be appreciated that it is a critical feature of the present invention that the ether oxygen and the X function comprising the acyl-X-methylether moiety of the subject prodrug compounds be separated by but a single carbon atom or methylene bridge. Otherwise, e.g., if the "methylene" linkage were ethylene or higher alkylene, such compounds would not be subject to the aforesaid chemical and/or enzymatic metabolism/hydrolysis and would not be facilely cleaved in vivo, into the noted non-toxic products of metabolism/hydrolysis. Hence, such ethylene and higher alkylene congeners are inoperative and not intended herein; indeed, same could not properly be deemed or designated as true "prodrugs".

While all of the compounds encompassed within the aforesaid generic formula (I) meet applicants' criteria, nevertheless certain compounds remain preferred, namely, the dipivalyloxymethyl, dihexanoyloxymethyl, diheptanoyloxymethyl, dioctanoyloxymethyl, di-n-dodecanoyloxymethyl, di-n-tetradecanoyloxymethyl, di-n-hexadecanoyloxymethyl, diacetyloxymethyl, dipentanoyloxymethyl, dibenzoyloxymethyl, dibenzoyloxybenzyl, dipropionyloxymethyl, dibutyryloxymethyl, benzoylaminomethyl, pivalylthiomethyl and dimethylaminoacetylaminomethyl derivatives of dobutamine, i.e., of 4-[2-[[3-hydroxyphenyl)-1-methylpropyl]amino]ethyl]-1,2-benzenediol, or 4-[2-[[3-p-hydroxyphenyl)-1-methylpropyl]-amino]ethyl]-pyrocatechol.

The following compounds are conveniently prepared utilizing those techniques above outlined:

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A compound selected from the group consisting of (a) those having the structural formula (I):

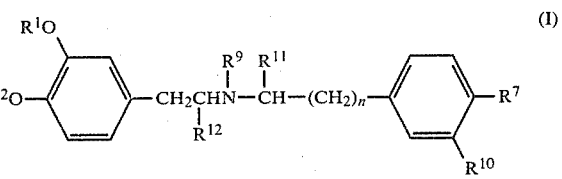

TABLE I

| Ex. | $R^1$ | $R^2$ | $R^7$ |
|---|---|---|---|
| 1 | $(CH_3)_3CCO_2CH_2-$ | $(CH_3)_3CCO_2CH_2-$ | $-OH$ |
| 2 | $(CH_3)_3CCONHCH_2-$ | $(CH_3)_3CCONHCH_2-$ | $-OH$ |
| 3 | $(CH_3)_3CCO_2CH_2-$ | $(CH_3)_3CCO_2CH_2-$ | $(CH_3)_3CCO_2CH_2-$ |
| 4 | $H_3CCH_2CO_2CH_2-$ | $H_3CCH_2CO-$ | $-OH$ |
| 5 | $(CH_3)_3CCO_2CH_2-$ | $-H$ | $-OH$ |
| 6 | $C_{12}H_{25}CO_2CH_2-$ | $C_{12}H_{25}CO_2CH_2-$ | $CH_3CO_2-$ |
| 7 | $C_6H_5CO_2CH(CH_3)-$ | $C_6H_5CO_2CH(CH_3)-$ | $-OH$ |
| 8 | $H_3CCH_2COSCH_2-$ | $H_3CCH_2COSCH_2-$ | $H_3CCH_2COSCH_2-$ |
| 9 | $C_6H_{11}CO_2CH_2-$ | $C_6H_{11}CO_2CH_2-$ | $-OH$ |
| 10 | $HOOC(NH_2)CH-CH_2CH_2-CO_2CH_2-$ | $HOOC(NH_2)CH-CH_2CH_2-CO_2CH_2-$ | $-OH$ |
| 11 | $\phi-CH=CH_2-COSCH(CF_3)-$ | $\phi-CH=CH_2-COSCH(CF_3)-$ | $-OH$ |
| 12 | $\phi-CO_2CH_2-$ | $\phi-CO_2CH_2-$ | $\phi-CO_2CH_2-$ |
| 13 | $H_3C(CH_2)_5CO_2CH_2-$ | $-H$ | $H_3C(CH_2)_5CO_2CH_2-$ |
| 14 | $(CH_3)_3CCO_2CH_2-$ | $(CH_3)_3CCO_2CH_2-$ | $-CONH_2$ |
| 15 | $(CH_3)_3CCO_2CH_2-$ | $(CH_3)_3CCO_2CH_2-$ | $-CONHCH_3$ |
| 16 | $(CH_3)_3CCO_2CH_2-$ | $(CH_3)_3CCO_2CH_2-$ | $-CO_2CH_3$ |
| 17 | $(CH_3)_3CCO_2CH_2-$ | $(CH_3)_3CCO_2CH_2-$ | $-CO_2C_2H_5$ |

From the foregoing, it will be appreciated that the prodrug derivatives according to invention exhibit all of the biological and therapeutic activity of their "parent" dobutamine drug species, for cardiotonic purposes, or for the treatment of any other disease state or condition responsive to dobutamine therapy, while at the same time being characterized by enhanced bioavailability and physiological availability, enhanced resistance to deterioration by air and light and to chemical attack, and even the ability to elicit the same pharmacological response as the parent drug form, but at lower dosages.

The dose of the prodrug administered, whether orally, intravenous solution, or the like, and whether a single dose or a daily dose, will, of course, vary with the needs of the individual. However, the dosage administered is not subject to definite bounds, but will usually be an effective amount, or the equivalent on a molar basis of the pharmacologically active form produced upon the metabolic release of the active, parent drug species to achieve its desired and physiological effect. See *Physicians' Desk Reference*, 31 (1977). Moreover, for any of the broad spectrum of dosage forms into which the subject prodrugs can be formulated, see *Remington's Pharmaceutical Sciences*, 14th Edition (1970).

wherein $R^1$ and $R^2$ are independently selected from the group consisting of hydrogen, $R^3$ —CO— and

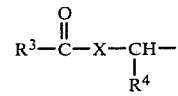

wherein X is O or S; $R^3$ is straight or branched chain alkyl having from 1 to 20 carbon atoms; aryl having from 6 to 10 carbon atoms; cycloalkyl having from 3 to 8 carbon atoms; alkenyl having from 2 to 20 carbon atoms; cycloalkenyl having from 4 to 8 carbon atoms; alkynyl having from 2 to 20 carbon atoms; or aralkyl, alkaryl, aralkenyl, aralkynyl, alkenylaryl, alkynylaryl, loweracyloxyalkyl, or carboxyalkyl, wherein alkyl, aryl, alkenyl and alkynyl are as defined above; $R^4$ is hydrogen, lower acyl, cyano, haloloweralkyl, carbamyl, loweralkylcarbamyl, diloweralkylcarbamyl, $-CH_2ONO_2$, $-CH_2OCOR^3$, or any member of the group defined by $R^3$ above; $R^7$ and $R^{10}$ are hydrogen, $OR^1$ or $OR^8$ wherein $R^8$ is lower alkyl, lower alkoxy, lower acyl, lower acyloxy, halo, haloloweralkyl, cyano, lower alkoxycarbonyl, lower alkylthio, amino, nitro, loweralkylamino, diloweralkylamino, carboxyl, carbamyl, loweralkylcarbamyl, diloweralkylcarbamyl or

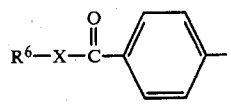

wherein $R^6$ is hydrogen or alkyl having from 1 to 10 carbons; $R^9$ is hydrogen, lower alkyl, $COCF_3$, $COOC(CH_3)_3$, $COOCH_2C_6H_5$, or other N-protective group; $R^{11}$ and $R^{12}$ are hydrogen or methyl; and n is 1 or 2; with the proviso that at least one $R^1$, $R^2$ or $OR^1$, when $R^7$ and/or $R^{10}$ is $OR^1$, must be $R^3COXCH(R^4)$- or $R^3COXCH(R^4)O$-, respectively; and (b) the non-toxic, pharmaceutically acceptable salts thereof.

2. A compound as defined by claim 1, wherein $R^7$ is hydroxy, $R^9$, $R^{10}$ and $R^{12}$ are hydrogen, $R^{11}$ is methyl and n is 2.

3. A compound as defined by claim 1, wherein $R^1$ and $R^2$ are $R^3COXCH(R^4)$—, $R^9$, $R^{10}$ and $R^{12}$ are hydrogen, $R^{11}$ is methyl and n is 2.

4. A compound as defined by claim 3, wherein X is O.

5. A compound as defined by claim 3, wherein X is S.

6. A compound as defined by claim 2, wherein either $R^1$ or $R^2$ is $R^3$—CO—.

7. A compound as defined by claim 2, wherein either $R^1$ or $R^2$ is hydrogen.

8. A compound as defined by claim 2, wherein $R^1$ and $R^2$ are $R^3COXCH(R^4)$—.

9. A cardiotonically effective composition of matter comprising a cardiotonically effective amount of a compound as defined by claim 1, and a pharaceutically effective carrier therefor.

10. The method of eliciting a cardiotonic sympathomimetic response in a warm-blooded animal, which comprises administering to such animal a cardiotonically effective amount of a compound as defined by claim 1.

11. The method of eliciting a cardiotonic sympathomimetic response in a warm-blooded animal, which comprises administering to such animal a cardiotonically effective amount of a composition of matter as defined by claim 9.

12. A compound as defined by claim 4, wherein $R^3$ is straight or branched chain alkyl having from 1 to 20 carbon atoms.

13. A compound as defined by claim 4, wherein $R^3$ is aryl having from 6 to 10 carbon atoms.

14. A compound as defined by claim 4, wherein $R^3$ is cycloalkyl having from 3 to 8 carbon atoms.

15. A compound as defined by claim 4, wherein $R^3$ is alkenyl having from 2 to 20 carbon atoms.

16. A compound as defined by claim 12, wherein $R^4$ is hydrogen.

17. A compound as defined by claim 12, wherein $R^4$ is haloloweralkyl.

18. A compound as defined by claim 12, wherein $R^4$ is alkyl.

19. A compound as defined by claim 12, wherein $R^7$ is $R^3COXCH(R^4)O$—.

20. A compound as defined by claim 8, wherein $R^3$ is straight or branched chain alkyl having from 1 to 20 carbon atoms.

21. A compound as defined by claim 8, wherein $R^3$ is aryl having from 6 to 10 carbon atoms.

22. A compound as defined by claim 8, wherein $R^3$ is cycloalkyl having from 3 to 8 carbon atoms.

23. A compound as defined by claim 8, wherein $R^3$ is alkenyl having from 2 to 20 carbon atoms.

24. A compound as defined by claim 20, wherein X is O.

25. A compound as defined by claim 24, wherein $R^4$ is hydrogen.

26. A compound as defined by claim 24, wherein $R^4$ is haloloweralkyl.

27. A compound as defined by claim 24, wherein $R^4$ is alkyl.

28. A compound as defined by claim 25, wherein $R^7$ is selected from the group consisting of aminocarbonyl, methylaminocarbonyl, methoxycarbonyl and ethoxycarbonyl.

* * * * *